(12) United States Patent
Milton et al.

(10) Patent No.: US 11,000,309 B2
(45) Date of Patent: May 11, 2021

(54) SAFETY SCALPEL

(71) Applicant: Medi-Safe Surgicals (Pty) Ltd, Somerset West (ZA)

(72) Inventors: Trevor John Milton, Somerset West (ZA); Norman Anthony Nieuwenhuizen, Boksburg (ZA)

(73) Assignee: Medi-Safe Surgicals (Pty) Ltd, Somerset West (ZA)

( * ) Notice: Subject to any disclaimer, the term of this patent is extended or adjusted under 35 U.S.C. 154(b) by 0 days.

(21) Appl. No.: 16/425,186

(22) Filed: May 29, 2019

(65) Prior Publication Data
US 2019/0365406 A1 Dec. 5, 2019

(30) Foreign Application Priority Data
May 31, 2018 (ZA) .................................. 2018/03615

(51) Int. Cl.
*A61B 17/3211* (2006.01)
*A61B 90/00* (2016.01)

(52) U.S. Cl.
CPC . *A61B 17/3211* (2013.01); *A61B 2017/32113* (2013.01); *A61B 2090/0801* (2016.02)

(58) Field of Classification Search
CPC .......... A61B 17/3211; A61B 17/32113; B26B 29/00; B26B 29/05; B26B 29/025; B26B 3/06
USPC ............................. D24/147; 606/167; 30/151
See application file for complete search history.

(56) References Cited

U.S. PATENT DOCUMENTS

| | | | | | |
|---|---|---|---|---|---|
| 3,905,101 | A | * | 9/1975 | Shepherd | A61B 17/3213 30/162 |
| 3,906,626 | A | * | 9/1975 | Riuli | A61B 17/3213 30/162 |
| 5,250,063 | A | * | 10/1993 | Abidin | A61B 17/3213 30/151 |
| 5,258,001 | A | * | 11/1993 | Corman | A61B 17/3211 606/167 |
| 5,417,704 | A | * | 5/1995 | Wonderley | A61B 17/3211 606/167 |
| 5,431,672 | A | * | 7/1995 | Cote | A61B 17/3211 606/167 |
| 5,556,409 | A | * | 9/1996 | Haining | A61B 17/3211 30/162 |
| 5,683,407 | A | * | 11/1997 | Jolly | A61B 17/3213 606/172 |

(Continued)

FOREIGN PATENT DOCUMENTS

| | | | |
|---|---|---|---|
| DE | 112018001281 T5 * | 11/2019 | ......... A61B 17/3211 |
| EP | 2672904 | 12/2013 | |

(Continued)

OTHER PUBLICATIONS

International Search Report and Written Opinion dated Aug. 26, 2019 for Intl. Patent Application No. PCT/IB2019/054481, filed May 30, 2019.

*Primary Examiner* — Jason Daniel Prone
(74) *Attorney, Agent, or Firm* — Knobbe, Martens, Olson & Bear, LLP

(57) ABSTRACT

A safety scalpel having a retractable protective guard for covering a blade of the scalpel when the scalpel is not in use is provided. The protective guard limits inadvertent contact with the scalpel blade which may reduce the likelihood of accidental cuts or damage to the blade.

13 Claims, 8 Drawing Sheets

(56) References Cited

U.S. PATENT DOCUMENTS

| | | | |
|---|---|---|---|
| 5,730,751 A * | 3/1998 | Dillon | A61B 17/3211 606/167 |
| 5,792,162 A * | 8/1998 | Jolly | A61B 17/3211 30/151 |
| 7,087,067 B2 * | 8/2006 | Kehr | A61B 17/3213 606/167 |
| 7,153,317 B2 * | 12/2006 | Kanodia | A61B 17/3211 606/167 |
| D535,026 S * | 1/2007 | Griffin | A61B 17/3211 D24/147 |
| 7,156,231 B1 | 1/2007 | Austria | |
| RE42,507 E * | 6/2011 | Wilkinson | B26B 29/025 606/167 |
| 8,931,181 B2 * | 1/2015 | Milton | A61B 17/3213 606/167 |
| 8,959,778 B2 * | 2/2015 | Baid | A61B 17/3213 30/151 |
| 9,027,254 B1 * | 5/2015 | Vodinh | A61B 17/3211 606/167 |
| 9,622,772 B2 * | 4/2017 | Hacker | A61B 17/3211 |
| 10,383,655 B2 * | 8/2019 | Rauchwerger | A61B 17/3211 |
| 2002/0143352 A1 * | 10/2002 | Newman | A61B 17/3213 606/167 |
| 2004/0236359 A1 * | 11/2004 | Shi | A61B 17/3213 606/167 |
| 2006/0212058 A1 * | 9/2006 | Djordjevic | A61B 17/3213 606/167 |
| 2006/0241664 A1 * | 10/2006 | Lam | A61B 17/3211 606/167 |
| 2010/0305593 A1 * | 12/2010 | Inzero | A61B 17/3213 606/167 |
| 2013/0079804 A1 * | 3/2013 | Milton | A61B 17/3213 606/167 |
| 2014/0157604 A1 * | 6/2014 | George | B26B 29/025 30/151 |
| 2015/0182247 A1 * | 7/2015 | Shi | A61B 17/3213 606/167 |
| 2015/0257777 A1 * | 9/2015 | Woodward | A61B 17/3211 606/167 |
| 2019/0314049 A1 * | 10/2019 | Shi | A61B 17/3211 |
| 2020/0121348 A1 * | 4/2020 | Milton | A61B 17/3211 |

FOREIGN PATENT DOCUMENTS

| | | | | |
|---|---|---|---|---|
| EP | 2915495 | | 9/2015 | |
| EP | 2757985 B1 * | | 1/2018 | A61B 17/3215 |
| GB | 2560382 A * | | 9/2018 | A61B 17/3211 |
| WO | WO 96/06571 | | 3/1996 | |
| WO | WO-2004002335 A1 * | | 1/2004 | A61B 17/3211 |
| WO | WO-2004045428 A1 * | | 6/2004 | A61B 17/3213 |
| WO | WO-2013041982 A3 * | | 6/2013 | A61B 17/3213 |
| WO | WO-2018163112 A1 * | | 9/2018 | A61B 17/3211 |
| WO | WO-2019229691 A1 * | | 12/2019 | A61B 17/3211 |

* cited by examiner

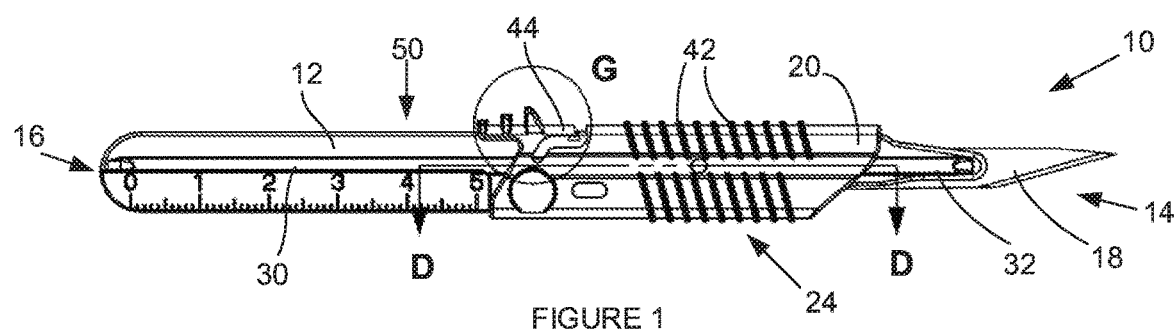
FIGURE 1
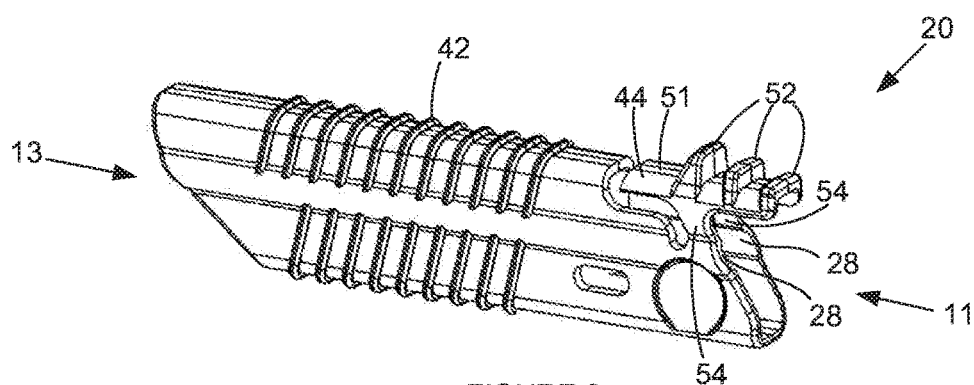
FIGURE 2
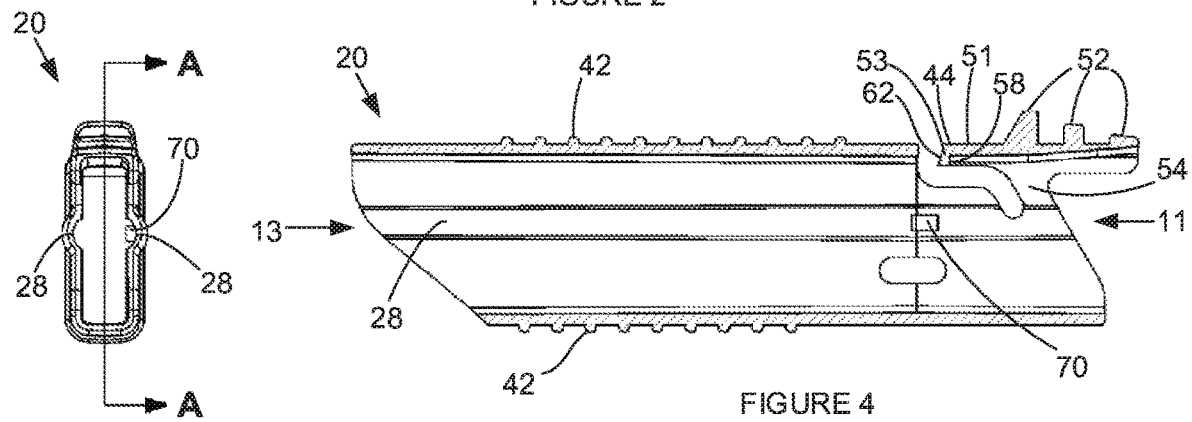
FIGURE 3
FIGURE 4
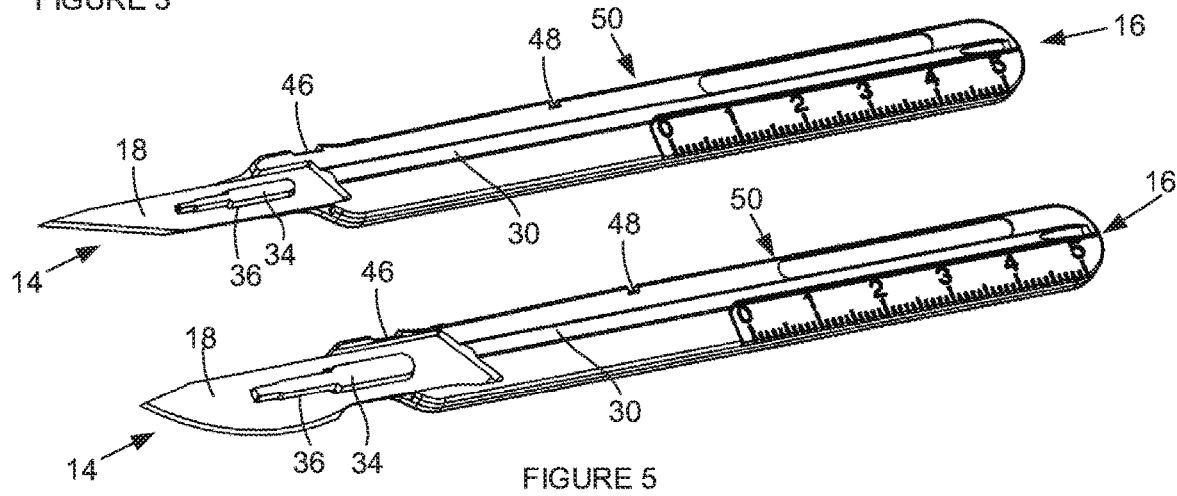
FIGURE 5

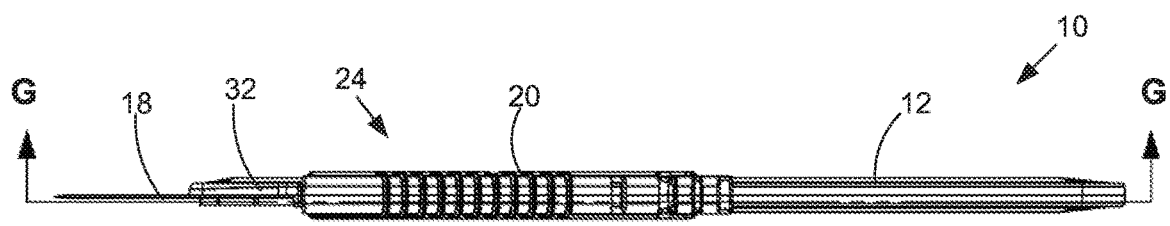
FIGURE 27
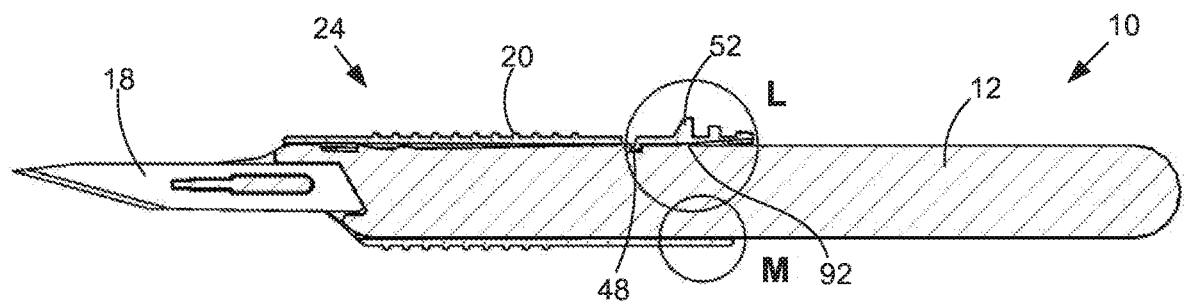
FIGURE 28
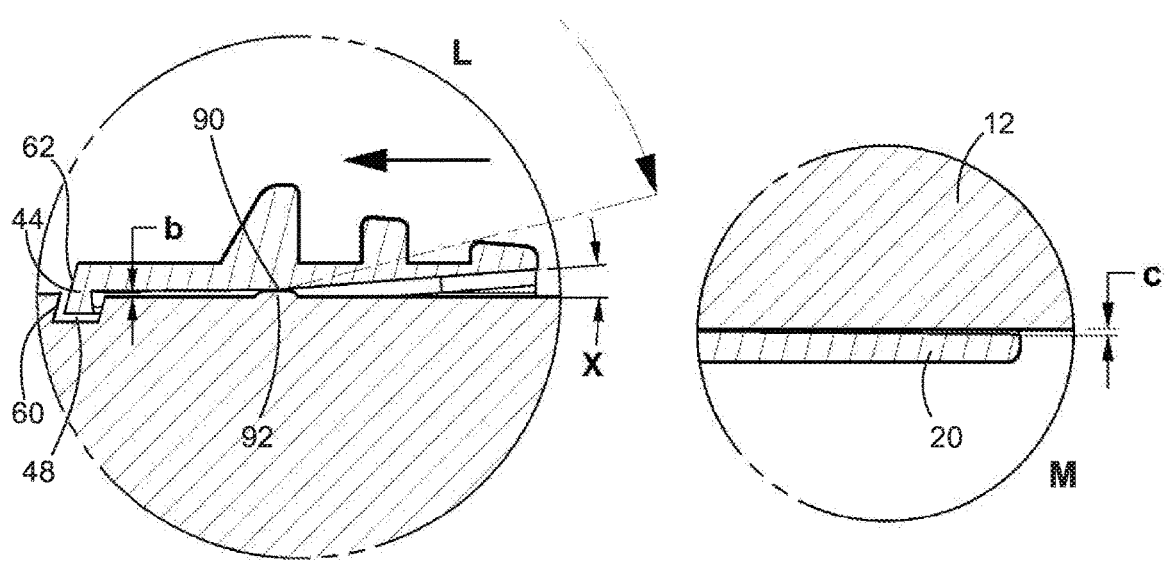
FIGURE 29
FIGURE 30

SAFETY SCALPEL

CROSS-REFERENCE TO RELATED APPLICATION

This application claims the benefit under 35 U.S.C. § 119 of South African provisional patent application number 2018/03615, filed on May 31, 2018, which is incorporated by reference herein.

TECHNOLOGICAL FIELD

This described technology relates to a safety scalpel of the type having a handle, a scalpel blade secured at a front end of the handle and a retractable protective guard. The protective guard is movable relative to the handle between an extended position in which it surrounds the scalpel blade during periods of non-use and a retracted position in which the scalpel blade is exposed for use.

DESCRIPTION OF THE RELATED TECHNOLOGY

The prevalence of infectious diseases such as HIV/AIDS and Hepatitis B and C have made needle stick injuries and accidental cuts from sharp surgical devices of major concern to health-care practitioners. Scalpels in particular have the potential to cause harm and transfer disease to healthcare workers when handled during or after surgery. This has led to the development and use of safety scalpels.

It is widely recognised that it is generally desirable for a scalpel to be provided with a guard that can be used to cover the scalpel blade when it is not in use; to expose the scalpel blade when it is required for use; and, as may be appropriate, to contain the scalpel blade for disposal purposes. Safety scalpels are single-use scalpels that fulfil these requirements. They typically include a blade, which is supported on an injection moulded plastic handle, and a protective guard for covering the blade when the scalpel is not in use. In many cases, the guard is reversibly retractable to permit a user to selectively expose the blade for use or cover it, as may be desired. Some of the drawbacks associated with these scalpels are that in many cases the protective guards are loosely secured to the handle and can become dislodged or inadvertently retracted during handling or disposal, thereby exposing the blade and presenting a cutting risk. Furthermore, some safety scalpels require two hands to operate the retractable protective guard, while others have mechanisms that are awkward to operate or which are prone to mechanical failure. A further problem associated with these scalpels is that the scalpel body or handle is often cut away to accommodate the protective guard. This may weaken the handle or impart excessive flex, posing a risk of the handle snapping during use, as well as reducing handling comfort and affecting the accuracy of incisions. A yet further problem associated with these types of scalpels occurs during manufacturing. Typically, the scalpels are assembled by first securing the blade to the handle, followed by attachment of the protective guard over the front end of the scalpel about the blade. This approach exposes the manufacturer to a risk of being cut by the scalpel blade and increases the likelihood of the blade being damaged during assembly through contact with the guard.

There is thus a need for a safety scalpel that can be employed in a manner having enhanced safety and which is capable of overcoming at least some of the aforementioned drawbacks associated with these types of scalpels.

The preceding discussion of the background to the described technology is intended only to facilitate an understanding of the present described technology. It should be appreciated that the discussion is not an acknowledgment or admission that any of the material referred to was part of the common general knowledge in the art as at the priority date of the application.

SUMMARY OF CERTAIN INVENTIVE ASPECTS

In accordance with a first aspect of this described technology there is provided a safety scalpel comprising a handle having a front end and a rear end with a blade secured at the front end, and a protective guard having a leading end and a trailing end and being slidably secured over the handle in a mounting zone of the handle within which the guard is manually operable between an extended position in which the guard projects forward of the front end to surround the blade, and a retracted position in which the guard is retracted from the front end to expose the blade for use, characterised in that the guard and handle are configured to permit securing of the guard to the handle by introduction of the leading end of the guard over the rear end of the handle followed by forward movement of the guard so that complementary securing formations on the guard and handle may be brought into cooperation to hold the guard captive in the mounting zone, the securing formations being configured to permit entry of the guard into the mounting zone and prevent removal of the guard therefrom.

Further features of the described technology provide for the handle and guard to include guide formations for guiding the guard onto the handle from the rear end; for the guide formations to include a co-operating groove and rail; for the rail to be provided on the handle and extend substantially along its length and for the groove to be provided on an inner surface of the guard, alternatively, for the groove to be provided on the handle and extend substantially along its length and for the rail to be provided on an inner surface of the guard; and for the handle to have a substantially consistent width and thickness along its axial length.

Still further features of the described technology provide for the handle and guard to be provided with co-operating tooth and notch formations that cooperate to releasably hold the guard in a "click-stop" manner in the retracted and extended positions; for notches to be associated with both the extended and retracted positions so that a "click-stop" is associated with each of the extended and retracted positions such that a person operating the scalpel will know exactly, by feel, and optionally also hearing, the position of the guard relative to the handle; for the tooth and notch formations to be adapted such that an audible "click" is created when a tooth formation engages a notch; and for the scalpel to have an extended terminal locked position defined by co-operating tooth and notch formations on the handle and guard, such terminal locked position being one in which the guard is located forwards of the normal extended position and from which it is substantially impossible to unlock the guard, at least for practical purposes.

Yet further features provide for the mounting zone to be defined between a forward end stop and a rearward end stop on the handle; for a guide channel to be provided between the end stops within which the tooth formation is slidably moveable; for the notches to be located within the guide channel; and for the complementary securing formations to be provided by the tooth formation and the forward and rearward end stops.

Even further features of the described technology provide for a manually releasable locking catch to be provided on the guard with a forward cooperating notch being provided on the handle for releasably locking the guard relative in the extended position and surrounds the blade; for the same manually releasable locking catch to be configured to be urged into tighter engagement with the forward cooperating notch during the application of a longitudinal force to the guard such as may be occasioned by contact with the front end thereof; for a rearward cooperating notch to be provided on the handle for engaging the manually releasable locking catch and releasably locking the guard relative to the handle in the retracted position in which the blade is exposed for use; and for the manually releasable locking catch to be configured to be urged into tighter engagement with the rearward cooperating notch during the application of a forward longitudinal force to the guard.

In accordance with a second aspect of this described technology there is provided a method of assembling a safety scalpel which includes a handle having a front end and a rear end with a blade secured at the front end and a protective guard having a leading end and a trailing end, the method comprising securing the guard to the handle by introducing the leading end of the guard over the rear end of the handle followed by forward movement of the guard to bring complementary securing formations on the guard and handle into cooperation to hold the guard captive in a mounting zone of the handle within which the guard is manually operable between an extended position in which the guard projects forward of the front end to surround the blade, and a retracted position in which the guard is retracted from the front end to expose the blade for use, wherein the securing formations are configured to permit entry of the guard into the mounting zone and prevent removal of the guard therefrom.

Certain embodiments of the described technology will now be described, by way of example only, with reference to the accompanying drawings.

BRIEF DESCRIPTION OF THE DRAWINGS

In the drawings:

FIG. 1 is a side view of the scalpel showing the protective guard in a retracted position exposing the blade for use;

FIG. 2 is a three dimensional perspective view of the protective guard shown in FIG. 1;

FIG. 3 is a cross-sectional view of the guard of FIG. 2;

FIG. 4 is a sectional view of the guard along the line A-A in FIG. 3;

FIG. 5 is a perspective view of a first side of two scalpel handles according to the present disclosure supporting scalpel blades of different sizes;

FIG. 27 is a top view of the scalpel with the guard in the retracted position;

FIG. 28 is a sectional view of the scalpel along the line G-G in FIG. 27;

FIG. 29 is a magnified view of the area indicated "L" in FIG. 28 showing in greater detail the locking catch in engagement with the rearward cooperating notch;

FIG. 30 is a magnified view of the area indicated "M" in FIG. 28 showing in greater detail the clearance gap between the guard and handle at a rearward periphery of the guard in the extended position;

DETAILED DESCRIPTION OF CERTAIN INVENTIVE EMBODIMENTS

Figure 6:
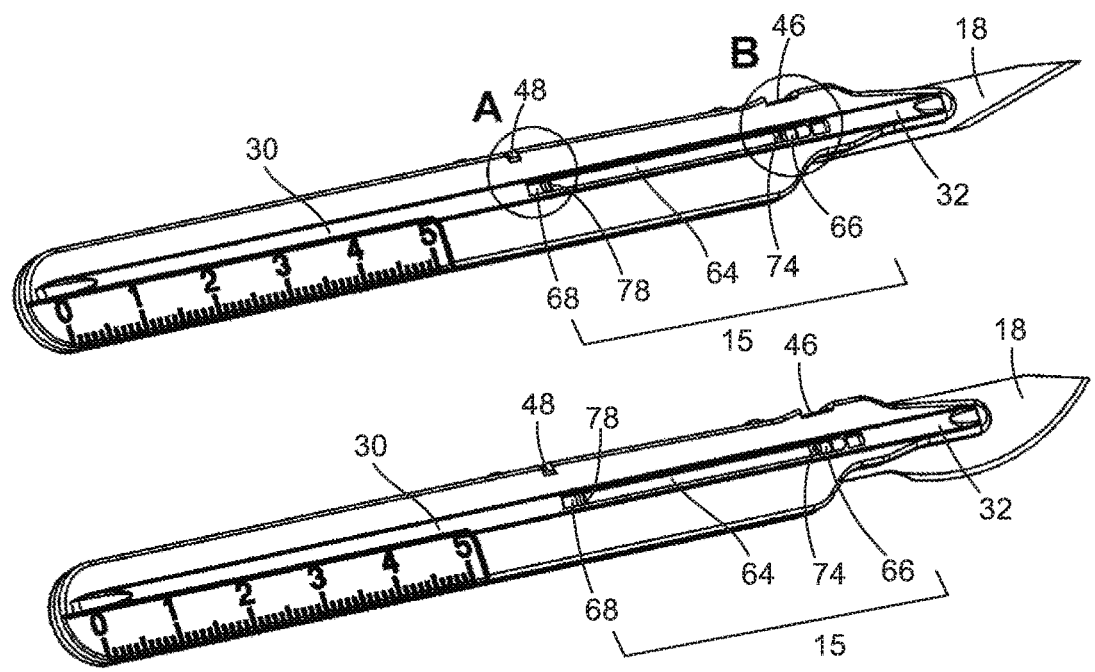
FIG. 6 is a perspective view of a second side of the scalpel handles of FIG. 5.
Figure 7:
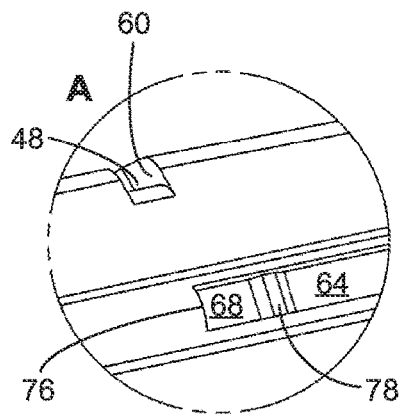
FIG. 7 is a magnified view of the area indicated "A" in FIG. 6 showing the second notch formation on the handle in greater detail.

A safety scalpel having a retractable protective guard for covering a blade of the scalpel when the scalpel is not in use is provided. The protective guard limits inadvertent contact with the scalpel blade which may reduce the likelihood of accidental cuts or damage to the blade.

In the embodiment of the described technology illustrated in FIGS. 1 to 30 of the drawings, a safety scalpel (10) comprises a handle (12) having a front end (14) and a rear end (16), a blade (18) secured at the front end, and a protective guard (20) having leading (11) and trailing (13) ends slidably secured in a mounting zone (15) of the handle. The guard is manually operable within the mounting zone between an extended position (22) in which the guard projects forward of the front end to surround the blade and thereby limit unintentional contact with the blade, and a retracted position (24) in which the guard is retracted from the front end to expose the blade for use. The scalpel is characterised in that the guard and handle are configured to permit securing of the guard to the handle by introduction of the leading end of the guard over the rear end of the handle followed by forward movement of the guard so that complementary securing formations on the guard and handle may be brought into cooperation to hold the guard captive in the mounting zone. The securing formations are configured to permit entry of the guard into the mounting zone and prevent removal of the guard therefrom. The handle has a substantially consistent width and thickness along its axial length, as shown in FIGS. 1, 5, 6, 9, 14, 21, 22, 27 and 28, to enable the guard to be secured to the handle from the rear end. The guard may be manufactured from a transparent or translucent material so that a user is able to view a position of the scalpel blade relative to the guard. This may serve to limit scalpel blade injuries and enhance the safety of the scalpel.

Guide formations on the handle and guard, which may be provided by co-operating grooves (28) and rails (30), are configured to guide the guard onto the handle from the rear end. In some embodiments, a rail may be provided on the handle and extend substantially along its length from the rear end to the front end, while a co-operating groove may be provided on an inner surface of the guard. In other embodiments, the rail may be provided on an inner surface of the guard and the groove provided on the handle. In the embodiment illustrated in the accompanying FIGS. 1-30, rails (30) are provided on each of two opposite sides of the handle and extend lengthwise therealong, as shown more clearly in FIGS. 5 and 6. An advantage of having the rails (30) extend along the length of the handle is that they provide flexural rigidity to the handle. However, the rails (30) need not necessarily extend along a length of the handle and may in some embodiments extend along only a portion of the handle. For effective operation of the guard, however, it is preferable that the rails extend along the mounting zone. The rails co-operatively engage a pair of opposing grooves (28) on opposite inner sides of the guard, as shown in FIGS. 2 to 4, to guide movement of the guard relative to the handle in an axial direction.

Figure 23:
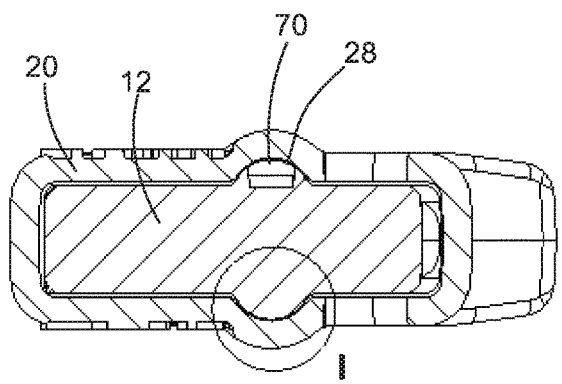
FIG. 23 is a is a cross-sectional view of the scalpel along the line F-F in FIG. 21.

As illustrated in FIGS. 5 and 6, the handle is elongate and substantially flat, having an approximately rectangular cross-section, as shown in FIG. 23. A longitudinally extending blade-supporting stem (32) is provided at the front end that merges with an elongate blade engaging lug (34) carried by the stem. The lug is adapted to cooperate with a longitudinal blade fitment window (36) in a scalpel blade through which the lug can pass obliquely. The blade can be fitted to the stem in a number of ways. In the embodiment illustrated in FIGS. 1, 5, 6, 22 and 28, the blade fitment window fits around the sides of the handle lug (34) and the operatively top edge of the lug (34) is heated by ultrasonic means or by induction heating to form a cap over the blade. This effectively welds the blade in position. As illustrated in FIG. 5, the blade supporting stem and lug can be configured to support scalpel blades of different sizes, including number 3 and number 4 blades [described according to code ISO 7740-1985 (E)], as are known in the art.

Figure 31:
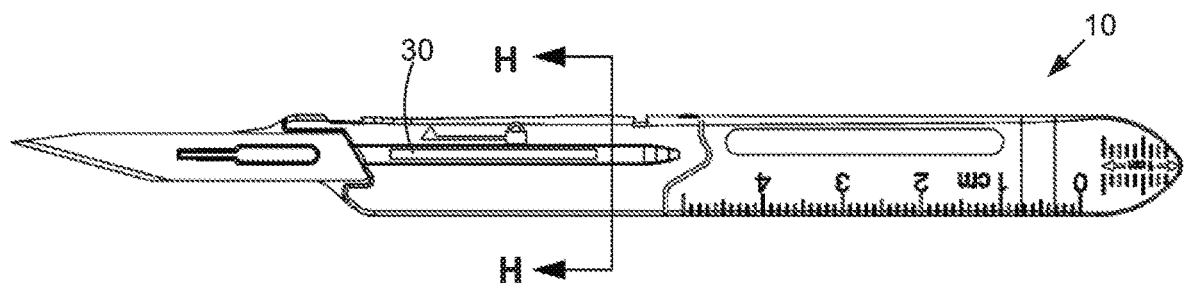
FIG. 31 is a side view of a first side of an embodiment of the scalpel (shown without guard) in which the rails are shortened and extend along the mounting zone and only partially along the handle.
Figure 32:
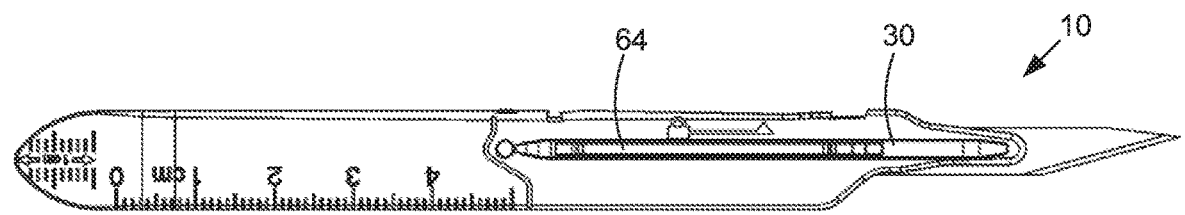
FIG. 32 is a side view of an opposite second side of the scalpel of FIG. 31 showing a shortened rail extending along the mounting zone.
Figure 33:
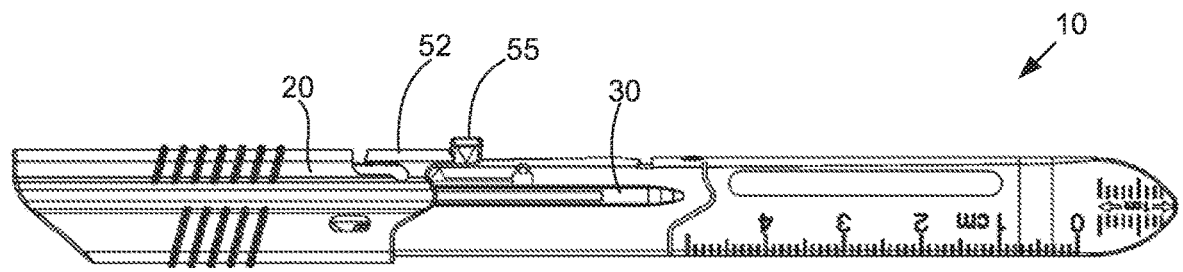
FIG. 33 is a side view of the embodiment of the scalpel shown in FIGS. 31 and 32 showing the guard in the extended position and an upwardly extending ridge on a rear end of the scalpel button.

A ruler is provided on both sides of the handle to allow a user to measure the length of an incision by holding the scalpel in either the left or the right hand, without having to change hands to measure, as may be required by scalpels having a ruler on only one side. Both rulers read from left to right with the ruler on the operatively left hand side of the handle having a zero position located away from the rear end of the handle and the ruler on the operatively right hand side having a zero position located proximate the rear end. The orientation of the zero positions of the two rulers with respect to the rear end provides a technical advantage allowing a user to measure an incision without having to turn the handle to orientate the ruler to read from left to right. Repositioning the handle in the hand, or rotating the handle with blade exposed could pose a danger to user and patient. In some other embodiments, however, rulers may be provided on both sides of the handle with zero positions proximate the rear end of the handle (as shown in FIGS. 31-33), or alternatively, with a ruler on the operatively left hand side having a zero position proximate the rear end and a ruler on the operatively right hand side having a zero position located away from the rear end.

Figure 13:
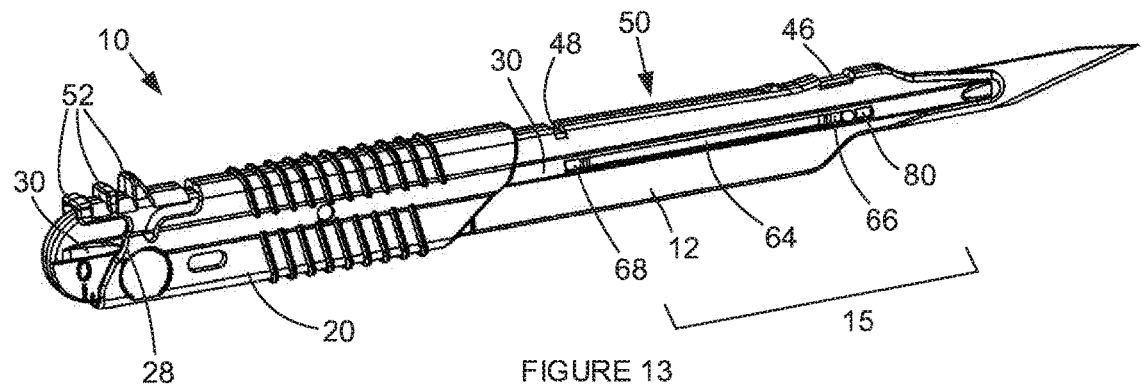
FIG. 13 is a three dimensional perspective view of the scalpel of FIGS. 1 and 9 showing the protective guard in the process of being coupled to the handle from the rear end.
Figure 14:
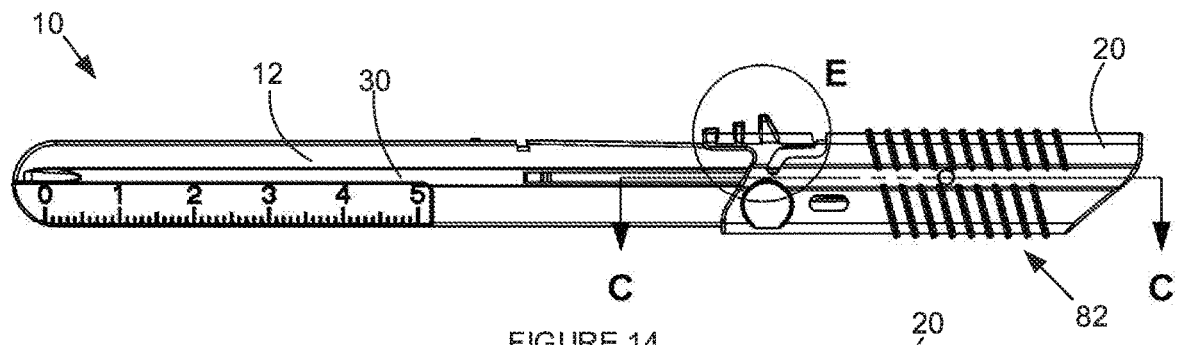
FIG. 14 is a side view of the scalpel showing the protective guard in the terminal locked position.

As illustrated in FIGS. 2 to 4, the tubular guard defines an elongate hollow channel which is substantially rectangular in cross section and includes a pair of longitudinally extending grooves (28) on opposing inner surfaces thereof, as shown in FIG. 3. Gripping formations (42) in the form of a plurality of parallel ribs extending substantially about an outer surface of the guard are provided to limit slipping when handling the guard. An integral manually releasable locking catch (44) is provided on the guard to engage forward (46) and rearward (48) cooperating notches provided on an operatively upper edge (50) of the handle in order to releasably lock the guard relative to the handle in the extended and retracted positions, respectively. In the embodiment of the scalpel illustrated in FIGS. 1, 2, 9, 11 and 16, the locking catch includes a convex top wall (51) having curved sides and a front end wall (53). The end wall includes angled front (62) and rear (58) surfaces that are shaped to engage front and back sides of the forward and rearward cooperating notches. As shown in FIGS. 5, 6 and 13, the forward cooperating notch is wider in an axial direction than the rearward cooperating notch to allow the locking catch to be urged forward unobstructed when in the extended position. The locking catch is carried by a manually operable button (52) that is connected to the main body of the guard by slightly sinuous connecting zones (54) that allow the locking catch to lift out of the forward and rearward cooperating notches when the button is operated. The button includes one or more ridges (55) on an operatively upper surface thereof for providing finger purchase when the button is actuated. The ridge can be positioned anywhere on the button, but is preferably located towards a rear thereof to provide for effective hinging. The ridge extends upwardly from an operatively upper surface of the button to provide a first point of contact with a user's finger or thumb and thereby provides a means of detecting by feel when the button has been contacted. The location of the ridge towards a rear position of the button serves to enhance a hinging force applied to the locking catch by downward pressure on the button. In some embodiments, a plurality of ridges may be provided, such as three ridges (as shown in FIGS. 1, 2, 4, 9 and 11, for example), which together provide a finger contact point. In the extended position, by exerting a generally rearward pressure on the button, the locking catch is raised and released from the forward cooperating notch to enable the guard to be slid rearwards to the retracted position in which it covers the adjacent part of the handle and exposes the blade for use. This movement is achieved by a flexing of the integral connecting zones and the positions of the button and catch into a disengaging position, as shown in dotted lines in FIG. 11. The arrangement is, however, such that the locking catch is urged into tighter engagement with the forward cooperating notch during the application of a longitudinal force to the guard, such as may be occasioned by contact with the front end of the guard when it is bumped or knocked. The forward cooperating notch has a rearward face (56) that is angled slightly forwards and configured to engage the angled rear surface (58) on the locking catch, such that in an engaged condition, when a force is exerted on the guard in the direction indicated by arrow "A" in FIG. 11, the catch is urged towards rotation in a direction indicated by arrow "B", that is, into firmer engagement with the notch. The cooperating angled faces of the locking catch and forward cooperating notch are thus geometrically arranged to prevent inadvertent de-latching of the guard. Inadvertent delatching, or exposing of the blade, of a moving guard type scalpel device may occur if the guard is forced backwards when the front end is pressed against a surface. A locking catch should only de-latch by deliberate manipulation of the button. In the present case, the guard will only de-latch when a downward and rearward finger force is exerted on the manually operable button. By reason of the rearward inclined angled face of the button, the hingable locking catch will hinge away from the entrapping influence of the angled face of the forward cooperating notch. Once the locking catch is clear of the forward cooperating notch, the guard is free to retract, under a continued rearward finger movement.

For safety scalpels having a moving protective guard it is considered advantageous that the guard be restrained from moving forward under a forward acting force, such as when the guard is held normally and a stabbing or lancing action is imparted to the blade. Should a typical scalpel design not provide for such a restraint, the guard may inadvertently move forward, thus covering the blade when such a stabbing or lancing action is carried out. To address this consideration, the rearward cooperating notch is provided with a front face (60) that is angled backwards and configured to engage the angled front surface (62) on the locking catch. When a forward acting force is applied to the guard, the locking catch is urged into firmer engagement with the rearward notch, in an analogous manner to its engagement with the forward notch, and the guard is hindered from sliding forward. The locking catch is hindered from inadvertently de-latching from the rearward cooperating notch by virtue of the abutting angled faces causing a self-locking or wedging action between the angled front surface of the locking catch and the front face of the rearward cooperating notch. Disengagement of the locking catch from the rearward cooperating notch can be effected by exerting a forward finger force on the manually operable button. By virtue of natural placement of the finger on the button, and the button geometry, a simultaneous downward force is imparted to the button thus causing the locking catch to hinge upwards and out of engagement with the rearward cooperating notch. Should the cooperating faces (60) and (62) be in contact, such as when a forward force is imparted to the protective guard, they will separate automatically, at the time the button is pressed forward, by virtue of their cooperating angled faces, causing a separation.

Figure 18:
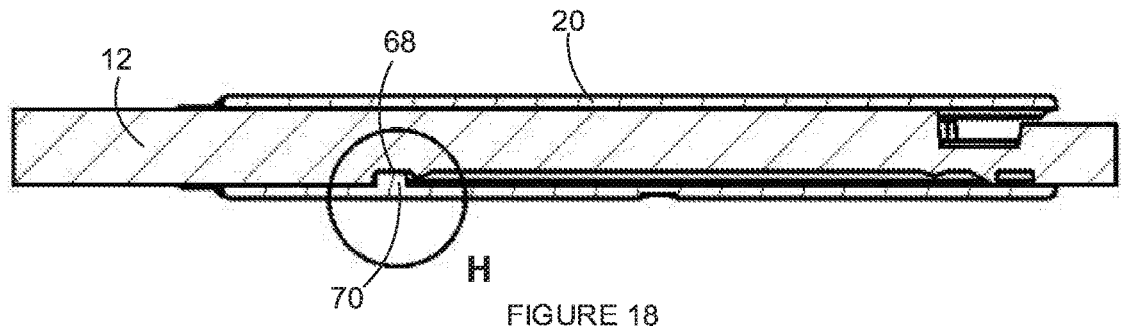
FIG. 18 is a sectional view of the front of the scalpel along the line D-D in FIG. 1 showing the guard in the retracted position and the tooth formation engaged with the second notch formation.
Figure 19:
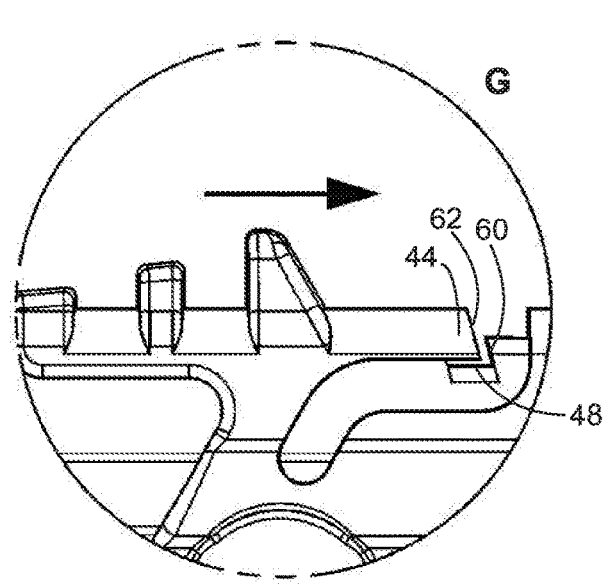
FIG. 19 is a magnified view of the area indicated "G" in FIG. 1 showing in greater detail the position of the locking catch when the guard is in the retracted position.
Figure 20:
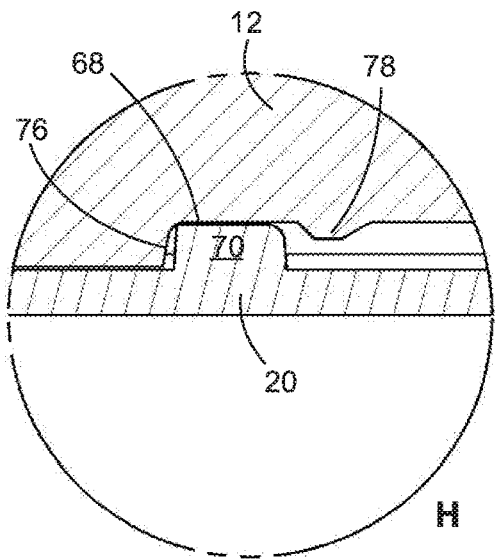
FIG. 20 is a magnified view of the area indicated "H" in FIG. 18 showing in greater detail the tooth formation engaged with the second notch formation when the guard is in the retracted position.
Figure 21:
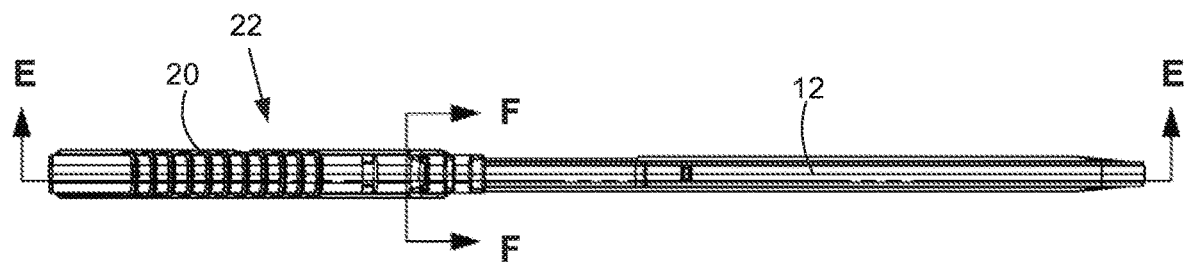
FIG. 21 is a top view of the scalpel showing the guard in the extended position.
Figure 22:
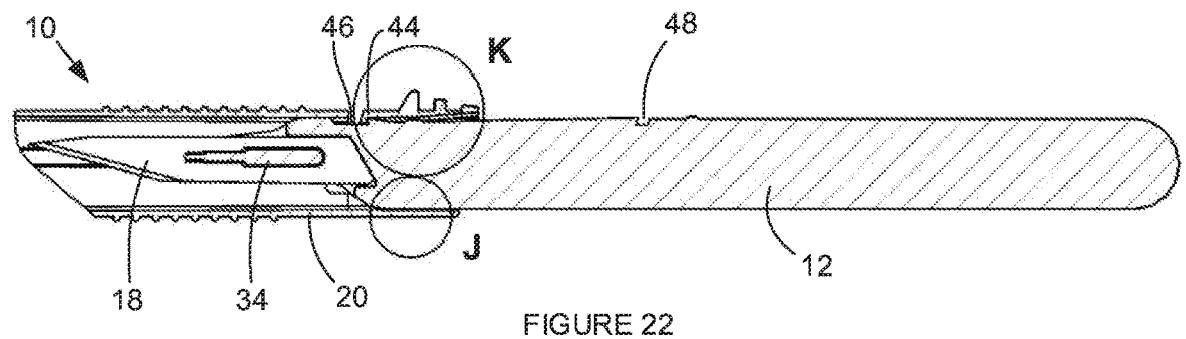
FIG. 22 is a sectional view of the scalpel along the line E-E in FIG. 21 showing the guard in the extended position.

As shown in the embodiment of the described technology illustrated in FIGS. 6 and 13, the mounting zone is defined between forward (72) and rearward (76) end stops on the handle and includes a guide channel (64) extending between the end stops. The mounting zone defines a region of the handle within which the guard is attached to the handle and slidable between the extended condition and the retracted position. The mounting zone can be located anywhere between the front and rear ends of the handle, but is usually located towards the front end. A position of the mounting zone can be selected to keep the guard in front of a hand held portion of the handle to prevent a user's fingers from getting in the way of the guard as is slides between the extended and retracted positions. In some embodiments, the mounting zone may generally correspond to a length of the guard, although in other embodiments the mounting zone may be longer or shorter than a length of the guard. The mounting zone may be substantially or completely occluded by the guard in the retracted position. The handle (12) and guard (20) are provided with tooth and notch formations that cooperate in a "click-stop" manner to releasably hold the guard selectively in the retracted or extended positions within the mounting zone. A first notch formation (66) associated with the extended position and a second notch formation (68) associated with the retracted position are located within the guide channel on a side of the handle. A cooperating tooth formation (70) located on an inner surface of the protective guard is slidably moveable within the guide channel. The tooth formation and forward and rearward end stops together form complementary securing formations that cooperate to hold the guard captive within the mounting zone. The first notch formation is defined between the forward end stop (72) of the guide channel and a forward detent ramp (74), as shown more clearly in FIGS. 6 and 8. Similarly, the second notch formation is defined between the rearward end stop (76) of the guide channel and a rearward detent ramp (78), as shown in FIGS. 18 and 20. The detent ramps have sloped leading and trailing sides to enable the tooth formation to slide thereover into or out of the notches as required. The tooth formation is configured to engage the respective notches and be releasably held captive therein when a sufficient forward or rearward force, as the case may be, is applied to the guard to overcome the restraint of the detent ramp and move the tooth formation into the notch formation. The tooth formation is liberated from the notch formation when a sufficient force is applied to the guard in an opposite direction to urge the tooth formation back over the ramp and out of the notch formation. The tooth and notch formations are adapted such that an audible "click" is created when the tooth formation engages and disengages a notch formation. These features permit a person operating the scalpel to know exactly, by feel, and optionally also hearing, the position of the guard relative to the handle.

The restraint of the guard in the extended and retracted positions, assisted by resilience of the guard side walls, imparts a minimal, momentary hold-back force to the guard once the locking catch is disengaged from the first and second notch formations and as the tooth formation overcomes the detent ramps. A minimal restraint is advantageous in order to assure that a positive, intentional directional force is applied to the finger-activated locking catch. A secondary effect of this mechanism is that it limits unnecessary, minor movement, or "rattle" of the guard, while in the extended and retracted positions. Such movement is due to clearance gaps between the guard and handle. Loose fitting components may be mistaken for poor quality or malfunction, thus, a mechanism that dampens or mitigates unnecessary movement without causing excessive resistance to normal sliding function is favourable.

Figure 8:
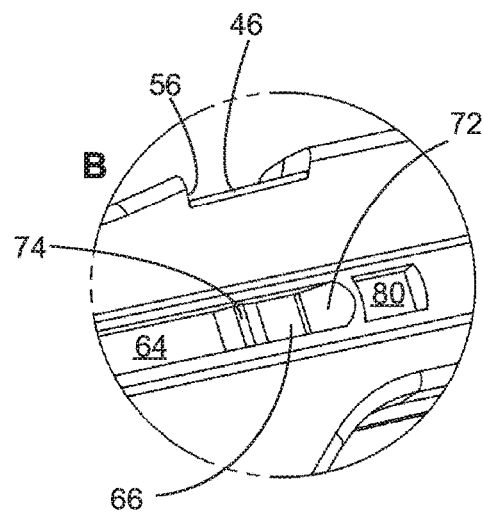
FIG. 8 is a magnified view of the area indicated "B" in FIG. 6 showing the first notch formation and terminal notch formation on the handle in greater detail.
Figure 9:
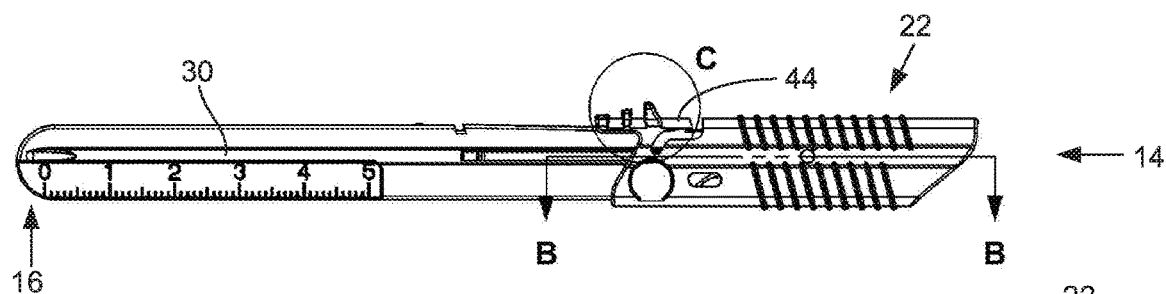
FIG. 9 is a side view of the scalpel showing the protective guard in an extended position surrounding the blade.
Figure 10:
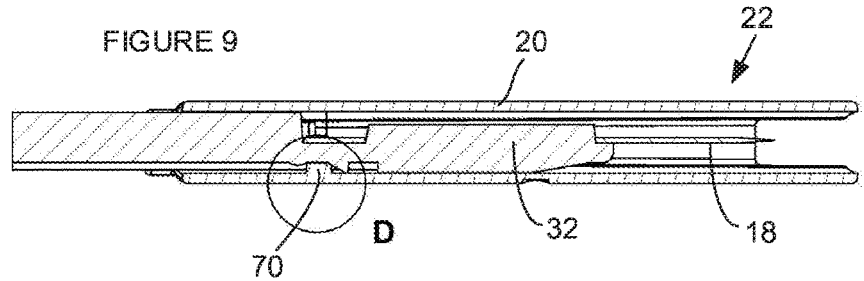
FIG. 10 is a sectional view of the front end of the scalpel along the line B-B in FIG. 9.
Figure 11:
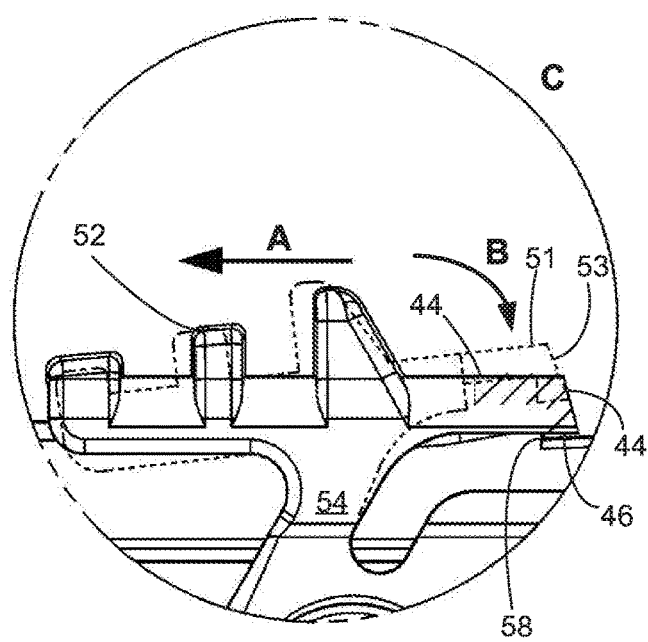
FIG. 11 is a magnified view of the area indicated "C" in FIG. 9 showing the hingeable locking catch in an engaged condition (solid lines) and a disengaged condition (broken lines) in greater detail.
Figure 12:
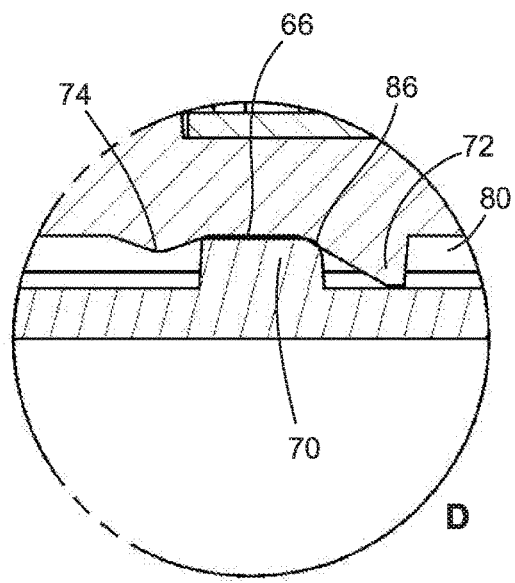
FIG. 12 is a magnified view of the area indicated "D" in FIG. 10 showing in greater detail the tooth formation engaged with the first notch formation.
Figure 15:
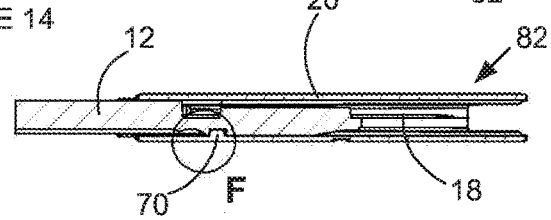
FIG. 15 is a sectional view of the front of the scalpel along the line C-C in FIG. 14 showing the guard in the terminal locked position.
Figure 16:
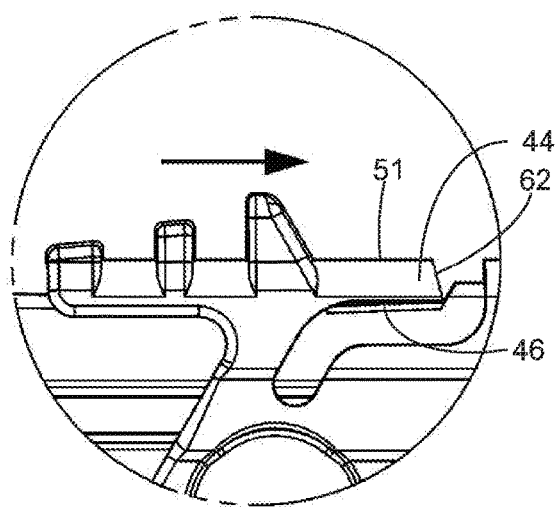
FIG. 16 is a magnified view of the area indicated "E" in FIG. 14 showing in greater detail the location of the locking catch relative to the forward cooperating notch when the guard is in the terminal locked position.
Figure 17:
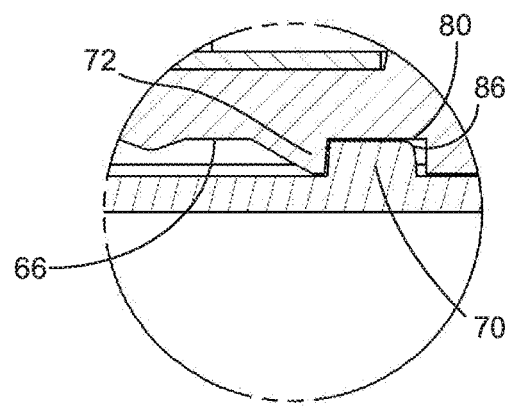
FIG. 17 is a magnified view of the area indicated "F" in FIG. 15 showing in greater detail the tooth formation engaged with the terminal notch formation.

A terminal notch formation (80) for locking the guard in an extended terminal locked position (82) is provided on the handle, forward of the first notch formation, as shown in FIGS. 13, 15 and 17. The forward end stop (72) of the first notch formation is ramped to enable the tooth formation to ride over the ramp and into the terminal notch formation when a sufficient force is applied to the guard to urge it forward of the extended position. The terminal notch formation defines a rectangularly shaped recess having sides which extend normally to the guide channel and which is shaped to receive the tooth formation and hold it captive therein in a non-releasable manner. The tooth formation is typically urged into the terminal notch formation after completion of a surgical procedure. The guard is returned from the retracted position to the extended position and then directly urged into the terminal locked position. As shown in FIGS. 8 and 16, the forward cooperating notch (46) is wide enough in an axial direction to permit the locking catch to move forward unobstructed when the guard is urged into the terminal position. The tooth formation abuts the first notch formation in the handle when the guard is in the extended position, as illustrated more clearly in FIG. 12. As the finger activated locking catch is moved forward from the extended position (shown in FIG. 16), the forward edge (86) of the tooth formation slides up the inclined face of the forward end stop under a resistive force due to resilience of the guard side walls. The guard continues to move forward under finger force, until the tooth formation becomes aligned with the terminal notch formation, at which time the tooth formation recoils into the terminal notch formation, producing a click sound. Once the co-operating tooth and notch formations associated with this position are engaged, it can be substantially impossible to unlock the guard from the terminal locked position or move it forward or backwards, at least for practical purposes.

The scalpel is assembled by securing the guard to the handle by introducing the leading end of the guard over the rear end of the handle followed by forward movement of the guard to bring the complementary securing formations on the guard and handle into cooperation. This serves to hold the guard captive in the mounting zone. The securing formations are configured to permit entry of the guard into the mounting zone and prevent removal of the guard therefrom. As the guard is coupled to the handle from the rear, the scalpel blade can be attached to the handle before coupling the guard and handle without the risk of the guard contacting the blade edge during assembly. Alternatively, the guard may be assembled to the handle in a temporary position along a rearward location on the handle, then the blade may be assembled, followed by a final sliding of the guard into its fully assembled position. Assembly of the guard to the handle from the front end after attachment of the blade could cause damage to the blade cutting edge or pose a cutting risk to the assembly worker. This latter method is commonly used to assemble most moving guard type safety scalpels in the art.

Figure 24:
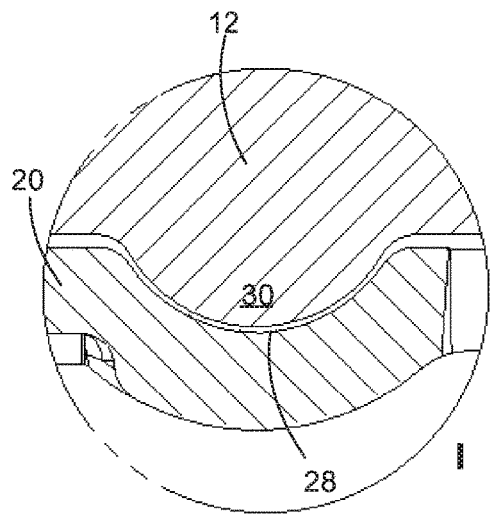
FIG. 24 is a magnified view of the area indicated "I" in FIG. 23 showing in greater detail the clearance gap between the handle and protective guard in the extended position.
Figure 25:
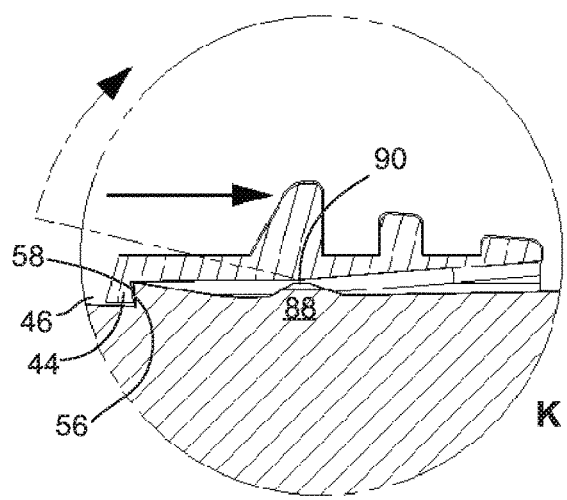
FIG. 25 is a magnified view of the area indicated "K" in FIG. 22 showing in greater detail the location on the handle of the pivot point and forward pivot block and the locking catch in engagement with the forward cooperating notch.
Figure 26:
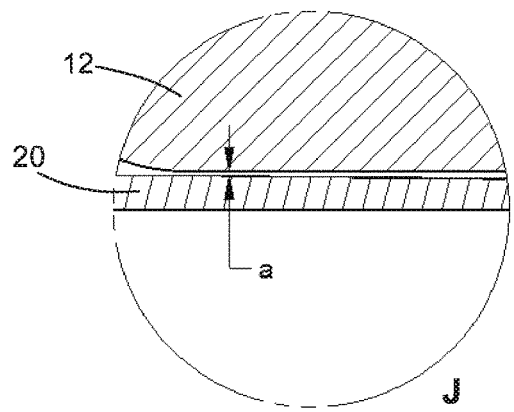
FIG. 26 is a magnified view of the area indicated "J" in FIG. 22 showing in greater detail the clearance gap between the handle and protective guard at an operatively lower edge thereof in the extended position.
Figure 34:
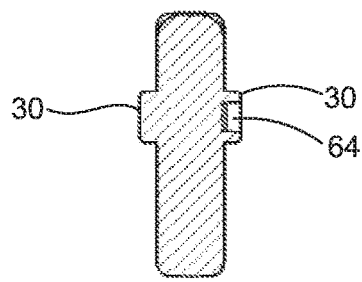
FIG. 34 is a section view along the line H-H in FIG. 31 showing the rails having a trapezoidal cross section.

The handle and guard of the scalpel are typically manufactured from injection moulded plastics. In order to render movement of the guard relative to the handle as effortless as possible, dissimilar plastic combinations may be employed in order to minimise sliding friction. For example, polycarbonate with acrylonitrile butadiene styrene (ABS), or polyoxymethylene with ABS. Numerous plastic material combinations may be used to improve sliding and decrease the force necessary to operate the device. Adequate clearances between the guard and handle are also selected to ensure free-sliding and to account for shrinkage variations due to moulding. Guidance of the guard along the length of the handle is at least in part effected through guide grooves (28) in the side walls of the guard component, in cooperation with rails (30) on the sides of the handle. Clearance gaps between the guide grooves (28) and rails (30) are also selected to facilitate minimal resistance to sliding. In the embodiment illustrated in FIGS. 2, 3, 13, 23 and 24, the guide grooves (28) have a curved side profile, although in other embodiments (as shown in FIGS. 31-34), the side profile may be trapezoidal or rectangular in side profile. In further embodiments, guide grooves on opposite sides of the handle may have different side profiles, for example, a curved guide groove on one side of the handle and a trapezoidal guide groove on the opposite side. The rails (30) are shaped to be complimentary to the shape of the guide grooves (28) so that where the guide grooves are curved in side profile, an outer surface of the rails (30) is also curved (as shown in FIGS. 23 and 24). Similarly, where the guide grooves are trapezoidal in side profile, the rails have a complimentary trapezoidal outer surface in side profile, as shown in FIG. 34.

Forward (88) and rearward (92) pivot blocks are located on the operatively upper edge (50) of the handle and associated with the extended and retracted positions, respectively, as shown in FIGS. 22, 25, 28 and 29. The pivot blocks are positioned to permit the locking catch to effectively pivot thereabout when disengaging the forward and rearward cooperating notches, respectively. Furthermore, action of the locking catch about the forward pivot block and the angled faces of the locking catch ensure that only a rearward force is necessary for de-latching in the rearward direction. The de-latching, as performed by finger or thumb action, is thereby made to be intuitive for a user. The forward hinge block (88), in cooperation with a pivot point (90) on the hingable locking catch performs a vital function in that it causes the guard to move upwards when in the extended position, thereby diminishing clearances between the guide grooves and rails (as shown in FIGS. 23 and 24), and also diminishing clearance between the guard and handle at an operatively lower edge of the handle, indicated as "a" in FIG. 26. This decreasing of sliding gaps causes an effective hinging movement, in that initial hinging of the locking catch does not have to take up any back-lash between the guard and handle. Once the guard is de-latched and rearward movement commences, the sliding gaps between guard guide grooves and handle rails are restored and the guard is able to slide backwards to the retracted position under minimal finger force.

When the guard is moved into the retracted position, the hingable latch pivot point (90) slides onto the rearward pivot block (92). This action causes the guard and locking catch to move upwards, thereby decreasing the gap (identified as "c" in FIG. 30) between guard and handle at an operatively lower edge thereof, and diminishing clearance between the guide grooves and rails. Clearance between an operatively top edge of the handle and a bottom face of the locking catch (identified as "b" in FIG. 29) is simultaneously increased to a small extent. In the action of the guard moving upwards slightly, it now presents with little or no lateral movement with respect to the handle. This condition is advantageous for effective de-latching of the guard from the rearward cooperating notch. Since there is no lateral movement of the guard with respect to the handle, when a finger or thumb is placed on the rearward portion of the locking catch and a forward movement imparted, the locking catch hinges upwards instantaneously, to a sufficient extent (indicated by pivot angle "x" in FIG. 29) to disengage the locking catch tip from the rearward cooperating notch. Once the guard is de-latched and forward movement commences, the sliding gap between guide grooves and rails is restored and the guard is able to slide forwards towards the extended position under minimal finger force. Importantly, as a result of the geometry of the button on the locking catch and the position of the pivot point relative to the position of finger placement on the locking catch, a forward imposed force from a finger placed on the button will cause the locking catch to naturally hinge upwards thus effecting delatching of the locking catch. This action is configured to be intuitive, in that an additional or simultaneous action is not necessary for de-latching.

It will be appreciated that many other embodiments of a safety scalpel exist which fall within the scope of the described technology. For example, guide formations in the form of tooth-like projections configured to cooperate with corresponding grooves may be provided on the handle and guard for guiding the guard onto the handle from the rear end or to guide the guard between the extended and retracted positions.

Furthermore, the scalpel may be manufactured from alternative materials to plastics and may, for example, include a wooden or metal handle or protective guard. In some embodiments, the scalpel handle may be manufactured from stainless steel, for example, by a metal injection moulding (MIM) process, to provide a weighted scalpel handle that may be preferred by some users. In these embodiments, the metal handled scalpel may be packaged in a disposable, single use form with a blade and cover assembled on the handle, in a similar manner to which a disposable plastic handled scalpel might be packaged.

Throughout the specification unless the content requires otherwise the word 'comprise' or variations such as 'comprises' or 'comprising' will be understood to imply the inclusion of a stated integer or group of integers but not the exclusion of any other integer or group of integers.

What is claimed is:

1. A safety scalpel comprising:
   a handle having a front end and a rear end with a blade secured at the front end the handle comprising:
      first securing formations including a forward end stop, a rearward end stop, and a guide channel,
      first and second notch formations,
      a forward cooperating notch; and
      a rearward cooperating notch; and
   a protective guard having a leading end and a trailing end, the protective guard comprising:
      second securing formations including a tooth configured to engage with the first and second notches and the guide channel, and
      a manually releasable locking catch,
   wherein the guard is slidably secured over the handle in a mounting zone defined between the forward end stop and the rearward end stop of the handle, the guard being manually operable between an extended position in which the first notch formation is engaged with the tooth and in which the guard projects forward of the front end to surround the blade, and a retracted position in which the second notch formation is engaged with the tooth and in which the guard is retracted from the front end to expose the blade for use, wherein the rearward cooperating notch is configured to engage the manually releasable locking catch in the retracted position,
   wherein the guard and handle are configured to permit securing of the guard to the handle such that, during assembly, the leading end of the guard is introduced over the rear end of the handle followed by forward movement of the guard so that the tooth is brought into cooperation with the forward end stop, the rearward end stop, and the guide channel to hold the guard captive in the mounting zone when the scalpel is not positioned in an extended terminal locked position, the first and second securing formations being configured to permit entry of the guard into the mounting zone,
   wherein the extended terminal locked position of the handle is defined by the first securing formations on the handle and the second securing formations on the guard,
   wherein in the extended terminal locked position the guard is located forwards of the extended position and it is substantially impossible to unlock the guard from the extended terminal locked position, and
   wherein the guard is further configured to be releasably locked in the extended position via operation of the manually releasable locking catch and the forward cooperating notch.

2. The safety scalpel as claimed in claim 1, wherein the handle and guard include guide formations for guiding the guard onto the handle from the rear end during assembly of the safety scalpel.

3. The safety scalpel as claimed in claim 2, wherein the guide formations include a co-operating groove and rail.

4. The safety scalpel as claimed in claim 3, wherein the rail is provided on the handle and the groove is provided on an inner surface of the guard.

5. The safety scalpel as claimed in claim 3, wherein the groove is provided on the handle and the rail is provided on an inner surface of the guard.

6. The safety scalpel as claimed in claim 1, wherein the handle has a width and thickness that is less than an inner width and thickness of the guard along a longitudinal axis of the safety scalpel.

7. The safety scalpel as claimed in claim 1, wherein the tooth and the first and second notch formations are further configured to operate in a "click-stop" manner in the retracted and extended positions.

8. The safety scalpel as claimed in claim 7, wherein the first and second notches are further configured so that a "click-stop" is associated with each of the extended and retracted positions.

9. The safety scalpel as claimed in claim 7, wherein the tooth and the first and second notches are adapted such that an audible "click" is created when the tooth engages one of the first and second notches.

10. The safety scalpel as claimed in claim 1, wherein the manually releasable locking catch is configured to be urged into engagement with the forward cooperating notch during the application of a longitudinal force to the guard.

11. The safety scalpel as claimed in claim 1, wherein the rearward cooperating notch is further configured to releasably lock the guard in the retracted position.

12. The safety scalpel as claimed in claim 1, wherein the manually releasable locking catch is located on a side of the guard that is different from the tooth.

13. The safety scalpel as claimed in claim 12, wherein the manually releasable locking catch is substantially symmetrical with respect to a plane defined by a longitudinal axis of the safety scalpel.

\* \* \* \* \*